United States Patent [19]

Huc et al.

[11] Patent Number: 4,670,014
[45] Date of Patent: Jun. 2, 1987

[54] IMPLANTABLE, BIOCOMPATIBLE RESERVOIRS PERMITTING CONSERVATION, CELLULAR CULTURING, OR CONTROLLED LIBERATION OF AN ACTIVE PRINCIPLE

[75] Inventors: Alain Huc, Sainte-Foy-Les-Lyon; Patrick Le Pivert, 2 rue Verdi, 06000 Nice; René Gimeno, Pelussin, all of France

[73] Assignees: Bioetica S.A., Lyons; Patrick Le Pivert, Nice, both of France

[21] Appl. No.: 703,884

[22] Filed: Feb. 21, 1985

[30] Foreign Application Priority Data

Feb. 21, 1984 [FR] France .................. 84 03180

[51] Int. Cl.⁴ .................................. A61K 9/22
[52] U.S. Cl. .................................. 604/891; 530/356
[58] Field of Search .................. 604/890–897; 260/123.7; 422/22

[56] References Cited

U.S. PATENT DOCUMENTS

| | | | |
|---|---|---|---|
| 2,738,429 | 3/1956 | Goldblith | 422/22 |
| 2,887,583 | 5/1959 | Emanuelson | 422/22 |
| 2,897,365 | 7/1959 | Dewey, II et al. | 422/22 |
| 3,014,024 | 12/1961 | Liberman et al. | 260/123.7 |
| 3,961,628 | 6/1976 | Arnold | 604/893 |
| 4,014,335 | 3/1977 | Arnold | 604/893 |
| 4,164,559 | 8/1979 | Miyata et al. | 604/894 |
| 4,344,431 | 8/1982 | Yolles | 604/892 |
| 4,347,234 | 8/1982 | Wahlig et al. | 424/15 |
| 4,351,337 | 9/1982 | Sidmar | 604/892 |
| 4,409,332 | 10/1983 | Jefferies et al. | 260/123.7 |
| 4,424,208 | 1/1984 | Wallace et al. | 260/123.7 |
| 4,450,150 | 5/1984 | Sidman | 604/891 |
| 4,451,397 | 5/1984 | Huc et al. | 260/123.7 |

OTHER PUBLICATIONS

Rubin et al., Collagen as a Vehicle for Drug Delivery in: The Journal of Clinical Pharmacology, Aug.-Sep., 1973, pp. 309–312

*Primary Examiner*—C. Fred Rosenbaum
*Assistant Examiner*—Jerome R. Smith, Jr.
*Attorney, Agent, or Firm*—Karl F. Ross; Herbert Dubno

[57] ABSTRACT

Biocompatible reservoirs are constituted by collagen, optionally associated with mucopolysaccharides and/or gelatin; these reservoirs can be filled with an active principle which does not have to be mixed with collagen. The reservoirs can be employed to either hold or to emit one or more active principles in order to concentrate same and/or to distribute same at a controlled rate "in vitro" and/or "in vivo". The reservoirs thus are enclosed vessels of conseration of "in vitro" or "in vivo" cultures of cells, bacteria or viruses.

3 Claims, 1 Drawing Figure

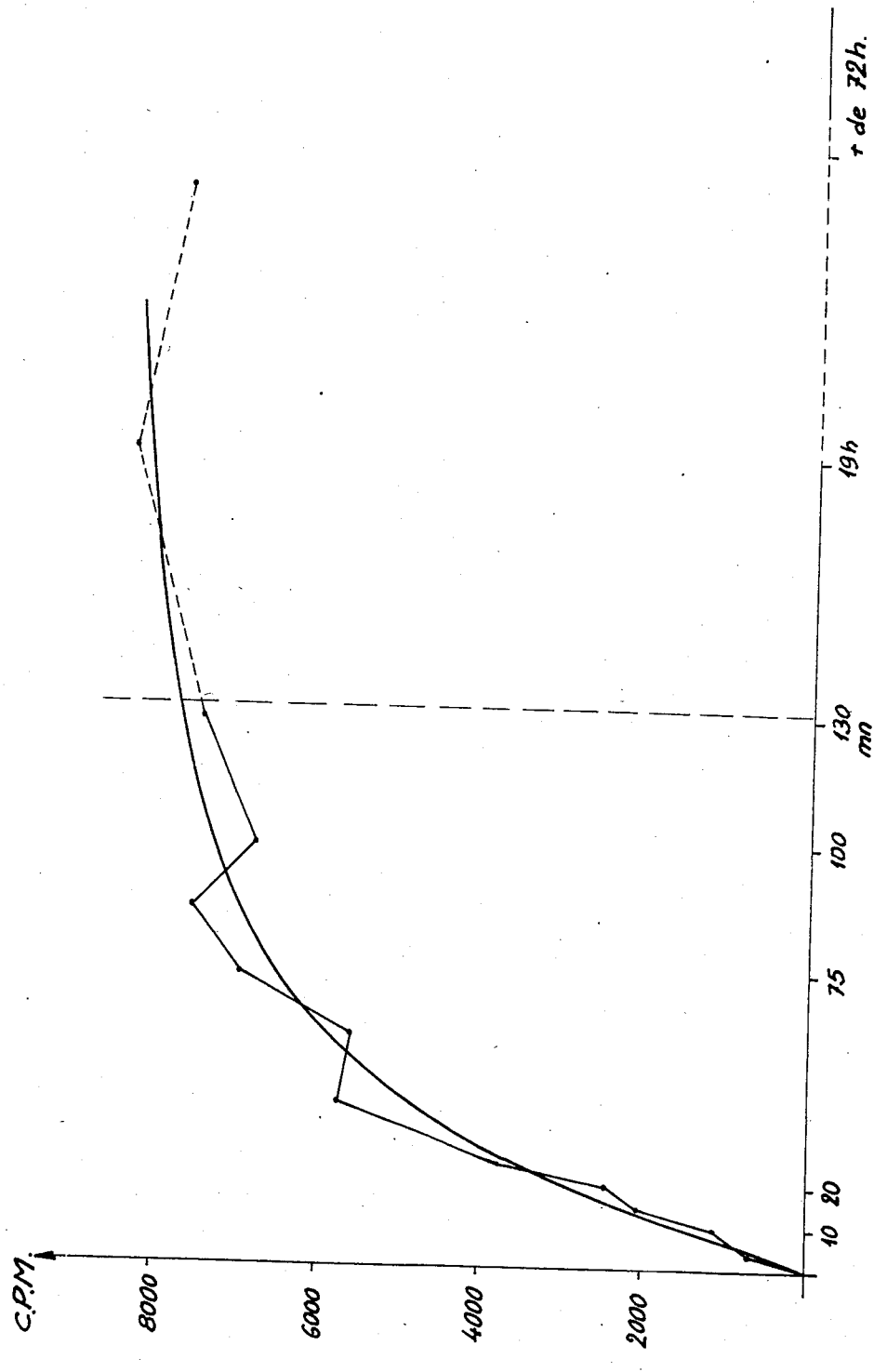

IMPLANTABLE, BIOCOMPATIBLE RESERVOIRS PERMITTING CONSERVATION, CELLULAR CULTURING, OR CONTROLLED LIBERATION OF AN ACTIVE PRINCIPLE

FIELD OF THE INVENTION

The present invention relates to implantable, biocompatible, reservoirs based on collagen which permit the conservation and/or the cellular culturing and/or the controlled liberation of an active principle.

BACKGROUND OF THE INVENTION

Currently it is necessary in many therapeutic applications involving animals or humans in the field of cellular biology to make use of reservoirs capable of conserving, concentrating or distributing at a controlled rate, in vitro and/or in vivo, one or several active substances, and if the need arises, the creation in situ of a new product.

Equally needed are chambers for conservation and/or for cultures in vitro and/or in vivo of cells, living and dead, of bacteria, of viruses, etc.

These reservoirs are designed to play, in some cases, the role of a simple container, or of containers having active walls, in place of implants, and the desired functions according to its form and its biodegradability may be diverse. Finally in a more general fashion, the reservoirs must be able to play the part of captivating or transmitting a very complex regulating system to liberate one or several active substances (biocapture or bioreactor). See *Biofutur*, January 1984, Biofutur, S. A., Ed. 75007, Paris.

Containers made out of implantable plastic material are already known, especially those of the type "micropump" which permit passage through an organism at a controlled rate, of determined doses of an active substance. It is necessary to note that in all cases, these containers are only somewhat biocompatible, and are not biodegradable.

It has also been established (Huc, A. and Comte, Ph., 1983, *Biofutur*, No. 9, pp 53–55) that collagen is the substance of choice for the preparation of biomaterials. The protein which constitutes a support matrix for conjunctive tissue, also possesses remarkable mechanical properties, an excellent biocompatibility, and a biogradability which is optionally modifiable according to the particular goal that is desired.

The collagen molecule having a length of about 3000 Å and a width of about 15 Å is constituted by three peptide chains. Each chain has a mass of about 100,000 daltons, and is in helicoidal form. The axes of the helices extend helically around a common axis through the interior of the macromolecule. Between certain chains, there exist reticulated or cross-linked bonds. The ordered arrangement of the macromolecules between these peptide chains leads to formation of fibers.

The excellent mechanical properties of collagen are provided in large part, by the helicoidal structure and the reticulated bonds.

The antigenic character of collagen is also very low. Consequently, collagen originally from an animal does not provoke an action of rejection when applied in vivo to a human being, according to a study conducted by Takeda, U. et al. and appearing in the *Journal of Toxicology Sciences*, Vol. 7, Suppl. II, pp 63–91, (1982).

It is also possible to modify the permeability of a collagen membrane by a variety of treatments (Stenzel, K. H. et al., American Rev. Biophys. and Bioeng., Vol. 3, pp 231–253, 1954).

OBJECT OF THE INVENTION

The object of the invention is to provide biocompatible, implantable reservoirs which permit concentration and/or cellular culturing and/or the controlled liberation of an active principle, and which are constituted essentially by a continuous envelope of collagen, per se, or collagen associated with mucopolysaccharides and/or gelatin. These reservoirs can include an active principle without the latter having been mixed with collagen, that is the collagen is independent both physically and chemically of the active principle.

SUMMARY OF THE INVENTION

The process of fabricating the biocompatible reservoirs of collagen according to the invention are now described in detail.

Hides obtained from freshly slaughtered calves are washed with water. The hair and the subcutaneous tissue are mechanically eliminated by the aid of a splitting apparatus and only the skin is saved. The latter is then chopped and ground. The ground product is then washed with a phosphate-containing tampon at a pH of 7.8, then rinsed with deionized water. It is then placed in an active acid solution at a pH of 3.5. The dilution must be such that the concentration of collagen must be about 1.5%. The mixture is then homogenized by ultrasonic waves, then degassed by agitation under vacuum. The gel thus obtained is transformed into a film, especially according to the process described in French Pat. Nos. 1,596,789 and 1,596,790 or transformed into a tube by a process known per se, and especially by a process described in commonly assigned copening U.S. application Ser. No. 703,890 filed Feb. 21, 1985, which is entitled *Process for the Preparation of Collagen Tubes Especially Tubes of a Small Diameter*. The process in the copending application includes the following steps; extrusion in a cylindrical spinneret equipped with a central concentric tube designed to receive part of coagulation bath, the acid aqueous gel containing about 1.5% native collagen, followed by a coagulation of the internal and external walls of the tube in a coagulation bath containing about 70% acetone and 30% ammonia, followed by the drying of the tubes thus formed. The coalescence of the free particles of the film or tube is assured by pressing between two heated rollers at a pressure of 500 g/cm$^2$ at a temperature of 145° C. for 5 seconds. The mechanical characteristics of the solidified material thus obtained are as follows: tensile strength is 400 g/cm for a distance covering 3 mm.

The reservoirs are obtained in the form of rectangular pads beginning with two planar films of the same dimensions joined on all four sides. The cylindrical containers are obtained by joining the extremities of a tube. The reservoirs can also be obtained in various forms by molding at about 60° C. of the collagen films followed by joining of their edges.

When preparing the homogeneous collagen-mucopolysaccharides such as those obtained according to French Pat. No. 2,517,315, either the tubes or the films can be similarly transformed into reservoirs as mentioned hereinabove, and which present, with respect to the same elements containing collagen alone, an added conductivity.

In the case where the reservoirs must be supplied with very great mechanical properties, the collagen can be associated with other materials, especially synthetic polymers. Thus the collagen films can be reinforced by deposition of a matrix, synthetic or metallic, on a layer of collagen gel, followed by covering the obtained combination with a new layer of collagen gel. The sandwich thus formed is dried in a tunnel, according to the conditions mentioned in French Pat. Nos. 1,596,789 and 1,596,790.

The composite material thus obtained is then solidified as described hereinabove to form a reservoir. The reinforced collagen tubes can be fabricated by surrounding a first tube of collagen by a synthetic matrix and by fastening it with the aid of a biological glue of the type Tissucol ® to a second collagen tube of a diameter slightly larger than that of the first tube. The reservoir will be obtained by joining the free ends of the tubes.

The biocompatible reservoirs thus obtained can be subjected to different treatments especially in order to modify their permeability, in order to control the diffusion of the active substance which they must contain.

This if it is desired to diminish the permeability of the membrane, to improve its biocompatibility while augmenting its mechanical resistance, reticulation of the collagen is carried out by treatment in a stove at 80° C. for 48 hours under a vacuum (0.1 mm Hg).

On the other hand it may be desired to provide a system with low biodegradability. According to the techniques previously used to arrive at this objective, the collagen is treated by fixing different substances, in particular aldehydes, on the active groups of the protein. Thus the collagen loses some of its biological properties and this treatment risks the entrainment in vivo of calcified collagenous material. Additionally, the substances fixed to the active groups increase the risk of a detrimental effect exerted on the host organism.

According to the present invention the reactive groups of the collagen are blocked, without any foreign substances (different from the process disclosed in French Pat. No. 2,235,133) which would be capable of diffusion in the organism, by introducing azide groups into the molecule according to the following process:

The material is placed for 8 days in an acidic methanol solution (pure methanol plus 0.3 N HCl). As a result the acidic free carboxy groups of the collagen are methylated according to the following reaction.

Collagen-COOCH$_3$ + H$_2$O

The acid groups are those of aspartic acid or glutamic acid.

The material is next thoroughly washed with water and placed in a 1% aqueous solution of hyrazine. The methyl groups are then transformed into hydrazide groups according to the following reaction:

A treatment time of 4 to 5 hours is necessary in order to obtain the maximum number of transformed groups. The material is then thoroughly mixed with water and then subjected to the action of a solution of sodium nitrite in 0.3 N HCl. Thus one obtains the azide-substituted collagen according to the following reaction:

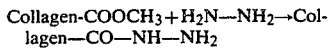

The total duration of this reaction is about 5 minutes. The material is then placed for about 2 hours in a borate tampon at a pH of 9 (boric acid, sodium tetraborate 0.2M) and then thoroughly mixed with water.

All of the process steps are carried out at ambient temperature (20° C.).

The tests carried out on the final material show that it contains no hydrazine, no sodium nitrite, and no other external substance.

Programmed differential calorimetry indicates that the denaturation temperature of collagen is about 10° C. higher for collagen thus treated than it is for untreated collagen or for collagen subjected to a simple reticulation process. Active collagen is thus more stable than reconstituted collagen. The denaturation temperature of the collagen thus prepared exceeds 37° C. normal body temperature. Thus the collagen will conserve all of its native structure, which is essential for its properties, especially mechanical properties. Furthermore the collagen treated according to the new invention is better resistant to the attack of proteolytic enzymes.

A film of collagen thus treated has been implanted in a rat, both intraperitoneally and subcutaneously. Its behavior in vivo has been compared to that of a film of raw collagen placed in the same position but not treated according to the present invention.

The results of the examination are as follows:

After 21 days, the raw film has vanished, whereas after 90 days, the active film of the invention is always identifiable.

Mesothelial cells exist on the two implants but their appearance is retarded on the active material and the cells develop there less well.

In order to diminish the permeability of the collagen to retard the diffusion of the active principle, a molecule of a high molecular weight can be grafted onto the surface of the collagen. Moreover the size of this molecule is important because it plays the role of barrier to the passage of a substance through the collagen membrane.

According to another method of carrying out the invention, an enzyme capable of acting in vivo, on a biosubstance which the reservoir is destined to receive is grafted onto the collagen. Thus the organism will have at its disposal, a new substance prepared extemporaneously in vivo.

The grafting process can be that for example described in French Pat. No. 2,235,133 which consists of immersing the collagen product in a mixture of methanol and acid for several hours at ambient temperature, rinsing the product with water, then plunging the product in a hydrazine bath for several hours, then treating the product obtained with a mixture of sodium nitrate and acid for several minutes, followed by washing with sodium chloride solution. The collagen product thus activated is immersed in an enzymatic solution at a pH of 9 for about 2 hours in order to form an enzymatically active collagen support.

The conductivity can be perceptibly increased by forming a wall constituted by two layers of collagen and then forming a sandwich by adding a layer of minced, finely divided carbon powder.

The biocompatible reservoirs can then be sterilized with a dose of 2.5 MRad of gamma rays. Such a treatment definitely inactivates all of the microorganisms, reticulates the collagen, and inhibits its action on blood coagulation.

The materials thus obtained are analyzed in three ways: chemical analysis, mass spectral analysis, and structural analysis according to the method of Huc, A. and Bartholin, F. (1978), *Review of the Pasteur Institute,* Lyon, 11, No. 2, pp 179-190.

The first analysis puts into evidence the degree of purity of the collagen, the second the degree of integrity of the collagen, peptide chain, and the third the degree of non-destruction of the helicoidal structure. All of these analyses demonstrate that the protein possesses all of the characteristics of collagen.

In addition the programmed differential calorimetry permits the determination of the thermostability of the native structure and from there the knowledge of the biodegradability of the biomaterial.

BRIEF DESCRIPTION OF THE DRAWING

FIG. 1, the sole figure in the application, is a graph which plots radioactivity in the C.P.M. emitted by a collagen reservoir which contains a radioactive substance, as a function of time.

PERMEABILITY

The permeability studies have been carried out on a 20% solution of glycerine placed in a collagen tube having walls of a thickness of 100 microns. In order to carry out this analysis, glycerine marked with carbon 14 has been diluted with glycerine not labelled with carbon 14. The tube utilized has been reticulated by the heat treatment as indicated above and the quantity of the solution used was 500 microliters.

The reservoir thus prepared has been mixed with 10 ml of water. The diffusion has been followed by measuring at known time intervals, the radioactivity of the bath contained in the reservoir. The evolution curve of radioactivity in C.P.M. of 200 microliters of solution contained in the reservoir as a function of time is given in FIG. 1. It can be stated that as in the case of glycerine, small molecules more soluble in water, will reach equilibrium in at most two hours as between the interior and exterior of the tube. The collagen reservoir thus exerted an inhibitory effect on the diffusion of the substance which it contained.

Biodegradability

The experiments carried out on the collagen films treated by the azideforming method described hereinabove has shown that the temperature of the start of the deactivation is increased by about 10° C. in relation to that of raw collagen, specifically from about 35° to 45° C. Under these conditions, the collagen in vivo will not lose its helicoidal structure and will conserve its mechanical properties.

Additionally, it has been established that a collagen reservoir implanted subcutaneously is not digested by the collagenases after 90 days. After about 3 weeks the collagen reservoir can be completely used up. Finally a more or less strong effect on the biodegradability can be obtained by modifying the contact time of the collagen, with the methyl alcohol in the first step of the treatment, to introduce the azide groups as mentioned above. A very short contact time results in the diminution of the number of azide blocking groups introduced and accordingly less protection for the collagen. The biodegradability of the reservoir will thus be greater than in the case where the azide treatment is complete.

Modification of the Permeability

A modification is obtained by varying the thickness of the collagen walls, by preparing the containers with a double wall, or by grafting molecules of a high molecular weight onto the collagen.

Employment of the Active Substances

The active substance can be placed in the interior of the reservoir, in the form of a solution or as a pure liquid. If a slower diffusion is desired, it is preferable to employ the active ingredient in the form of a powder or a lyophilisate.

In order to obtain very slow diffusion, the powders can be encapsulated in collagen according to the process described in French Patent Application 2,524,471. The substance can be included in a collagen sponge which itself is placed inside the reservoir.

The process described above is conducted in order to obtain a reservoir in the organism and which possesses various rates of degradation and which permits diffusion more or less rapidly in the organism. The two parameters will be fixed by the thickness of the walls, by the texture of the walls, and by the particular active principle in the reservoir.

The conditioning of the biocompatible reservoirs based on collagen according to the invention is not limited to films, tubes or containers, and it is evident that the invention equally embraces other forms of these systems such as balls, capsules, which are also capable of fulfilling the functions described hereinabove.

The applications of the biocompatible reservoirs according to the invention are numerous and varied; thus these reservoirs which are partially or totally biodegradable (optionally implanted in vivo) can be interposed, alone or in association with other captivating systems and/or regulators.

It is known that the percutaneous route permits undoubted advantages in the treatment of systemic diseases but that the employment of the classical gelanic forms with the goal of prolonged action often gives rather poor results. The major problems encountered are:

The difficult application of a precise dosage and the mediocre manageability of the paste or liquid form, which are troublesome for the patient, especially if ambulatory;

The difficulties with respect to the application surface on which the rate of penetration is dependent; and The important role of the mode of application since a rubbing of the skin can augment the resorption by local vasodilation.

The improvement in the biocompatible reservoirs which are derived from collagen according to the invention results in a solid, transdermal system which liberates a controlled amount of active principle. The active principle, in the exact dose, is dispersed in a liquid phase, diffused at a constant rate, predetermined in vitro for several days to traverse the collagen walls which play the role of a porous, semi-permeable membrane; thus the intra- and inter-individual variables are avoided such as the age of the skin and the site of the application.

The biocompatible reservoirs according to the invention can be employed in the form of a hollow capsule composite of the type called "Tubepatch" of which one part is attachable to the skin, and the other part is surface active and also attached to the skin.

Among the many active principles that it is possible to liberate with the aid of the biocompatible reservoirs based on collagen according to the invention, one can specifically mention trinitrin, scopolamine, ephedrine, antiinflammatory agents, cicatrizants, cleansing agents, antibiotics, anesthetics or analgesics, without regarding this list in any way as limitative.

The biocompatible reservoirs according to the invention can be equally applied through a natural body opening for example vaginally; or through the uterus, or can even be applied intra-tumorally to provide in situ chemotherapy.

The reservoirs can be administered intravascularly for example in order to induce veinous schlerosis; the active principle in that case can be a glucose solution having a varying percentage of glucose so that the optimum percentage can be determined. Or by employing a lesser percentage of the sclerotic agent, a more sure sclerotic effect can be obtained by reason of the prolonged contact with the wall, with as a supplemental advantage, the biodegradability and the absence of toxicity of the material.

The use of the biocompatible reservoirs according to the invention may be used in preparing artificial pancreases. The advantage here is that the reservoirs are impermeable to antibodies and lymphocytes but permeable to insulin and glucose, needed by the cells to live and function.

Another method of applying the biocompatible reservoirs according to the invention is as containers and as micro-implants for living cells.

The reservoirs may be used as cell container, for congealing and/or lyophilizing, in order to permit the treatment of living cells, previously eradicated from healthy tissues or from tumors of cultivated cells.

The walls of the biodegradable containers more or less rapidly permit, after implantation, in vivo, the liberation of active principles on the one hand, and on the other hand their permeability ensures nutrition in vivo (pancreatic cells, thyroidal cells, osteoblasts, blood cells, placental cells, sperm cells, ovules, etc).

Thus the containers can serve as recipients in the retention, conservation, transport and transplantation of viable cells; they protect their contents against the attacks of the organism while permitting the discharge of the active principle into that organism.

Finally the containers can serve as selective captivation devices for biological substances (for the selective fixation of antigens or antibodies).

It is evident that the applications mentioned above are not limitative and that the field of application of the biocompatible reservoirs is vast since it is possible with the elements of the system, collagen alone or associated with mucopolysaccharides and/or gelatins provides a membrane that is permeable and a biodegradability that is fixed according to the particular fabrication method; as well as the role played by a number of variables such as functional groups, the form of the containers, the type of active principle and the place of implantation.

We claim:

1. A reservoir which is at least partially biocompatible and implantable which permits conservation, cellular culturing or controlled liberation of an active principle, said reservoir comprising a continuous envelope containing collagen which is filled with an active principle, wherein the envelope consists essentially of native collagen whose reactive carboxy groups have been blocked by introducing azide groups thereon, wherein the active principle which fills the collagen reservoir is independent of the collagen, and wherein the collagen has reduced biodegradability.

2. A reservoir which is at least partially biocompatible and implantable which permits conservation, cellular culturing or controlled liberation of an active principle, said reservoir comprising a continuous envelope containing native collagen and which is filled with an active principle, wherein the collagen of the envelope has a molecule of high molecular weight grafted onto its surface, and wherein the active principle which fills the collagen reservoir is independent of the collagen, and wherein the collagen has reduced permeability.

3. A reservoir which is at least partially biocompatible and implantable which permits conservation, cellular culturing or controlled liberation of an active principle, said reservoir comprising a continuous envelope containing native collagen and which is filled with an active principle, wherein the collagen envelope is grafted onto an enzyme with is capable of reacting in vivo with the active principle contained in the collagen envelope and wherein the active principle which fills the collagen reservoir is independent of the collagen.

* * * * *